United States Patent [19]

Thomas et al.

[11] 4,328,029
[45] May 4, 1982

[54] N-PYRIMIDINYLMETHYL-HALOACETANILIDE COMPOUNDS AND HERBICIDAL COMPOSITIONS

[75] Inventors: Rudolf Thomas; Jörg Stetter, both of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 171,784

[22] Filed: Jul. 24, 1980

[30] Foreign Application Priority Data

Aug. 11, 1979 [DE]  Fed. Rep. of Germany ....... 2932643

[51] Int. Cl.³ ..................... A01N 9/22; C07D 239/34
[52] U.S. Cl. ....................................... 71/92; 544/242; 544/319; 544/334; 544/335
[58] Field of Search ................. 544/319, 334, 335; 71/92

[56] References Cited

U.S. PATENT DOCUMENTS

| | | | |
|---|---|---|---|
| 3,118,889 | 1/1964 | Schroeder | 544/242 |
| 3,442,945 | 5/1969 | Olin | 71/88 |
| 4,094,990 | 6/1978 | Hubele | 544/335 |
| 4,098,895 | 7/1978 | Hubele et al. | 544/335 |
| 4,272,282 | 6/1981 | Hansen et al. | 71/92 |

*Primary Examiner*—Anton H. Sutto
*Assistant Examiner*—James H. Turnipseed
*Attorney, Agent, or Firm*—Felfe & Lynch

[57] ABSTRACT

N-pyrimidinylmethyl-haloacetanilides of the general formula

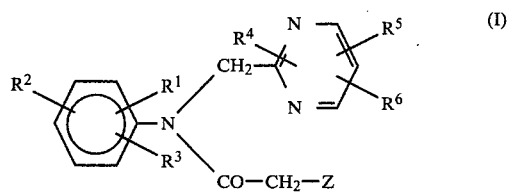

in which
R¹ represents hydrogen or alkyl,
R² represents hydrogen or alkyl,
R³ represents hydrogen or alkyl,
R⁴ represents hydrogen, alkyl, halogen, alkoxy or hydroxyl,
R⁵ represents hydrogen, alkyl, halogen, alkoxy or hydroxyl,
R⁶ represents hydrogen, alkyl, halogen, alkoxy or hydroxyl and
Z represents halogen,
and their use as herbicides.

35 Claims, No Drawings

N-PYRIMIDINYLMETHYL-HALOACETANILIDE COMPOUNDS AND HERBICIDAL COMPOSITIONS

This invention relates to certain new N-pyrimidinylmethyl-haloacetanilide compounds, to herbicidal compositions containing them, and to methods of combating undesired vegetation utilizing such compounds.

It is known that 2,6-diethyl-N-methoxymethyl-chloroacetanilide can be used for selectively combating weeds (see R. Wegler, Chemie der Pflanzenschutz- and Schädlingsbekämpfungsmittel (Chemistry of Plant Protection agents and Agents for Combating Pests), volume 5, page 255, Springer-Verlag (1977) and U.S. Pat. No. 3,442,945). This compound chiefly has an action against millet-like grasses, for example Digitaria, Echinochloa and the like. Other harmful grasses, for example Alopecurus, are combated by the above active compound only in relatively high dosages. However, significant damage to the crop plants, for example to sugar beet, occurs at these dosages, so that the active compound cannot be employed in this crop.

The present invention now provides, as new compounds, the N-pyrimidinylmethyl-haloacetanilides of the general formula

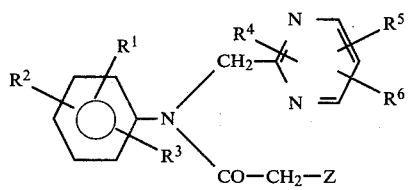

in which
$R^1$ represents hydrogen or alkyl,
$R^2$ represents hydrogen or alkyl,
$R^3$ represents hydrogen or alkyl,
$R^4$ represents hydrogen, alkyl, halogen, alkoxy or hydroxyl,
$R^5$ represents hydrogen, alkyl, halogen, alkoxy or hydroxyl,
$R^6$ represents hydrogen, alkyl, halogen, alkoxy or hydroxyl and
Z represents halogen.

The invention also provides a process for the preparation of an N-pyrimidinylmethyl-haloacetanilides of the formula (I) in which an N-pyrimidinylmethylaniline of the general formula

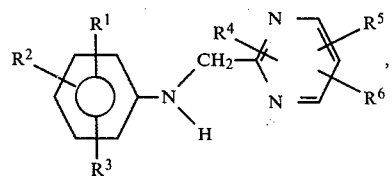

in which
$R^1$, $R^2$, $R^3$, $R^4$, $R^5$, and $R^6$ have the meanings indicated above,
is reacted with a haloacetic acid chloride, bromide or anhydride of the general formula

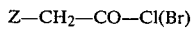  (IIIa) or $$(Z-CH_2-CO)_2O \quad (IIIb),$$

in which
Z has the meaning indicated above,
in the presence of a diluent and if appropriate in the presence of an acid-binding agent.

It has also been found that the N-pyrimidinylmethyl-haloacetanilides of the formula (I) have powerful herbicidal properties, in particular also selectively herbicidal properties.

Surprisingly, while having a very good herbicidal action, the N-pyrimidinylmethyl-haloacetanilides according to the invention exhibit, in particular, better possibilities for use as agents for selectively combating weeds in important crop plants than 2,6-diethyl-N-methoxymethyl-chloroacetanilide, which is known from the state of the art and is an active compound of high activity and the same type of action. The active compounds according to the invention are more effective against grasses such as Alopecurus and Poa than the comparison compound mentioned. In particular, they are tolerated by beet to a significantly greater extent than 2,6-diethyl-N-methoxymethyl-chloroacetanilide. In contrast to 2,6-diethyl-N-methoxymethyl-chloroacetanilide, which is known, it is thus possible, using the substances according to the invention, to combat grasses such as Alopecurus and Poa and millet-like grasses such as Digitaria, Echinochloa and Setaria simultaneously in beet, and also in cotton and soya bean. The substances according to the invention thus represent a valuable enrichment of the art.

The formula (I) provides a general definition of the N-pyrimidinylmethyl-haloacetanilides according to the invention. Preferably, in this formula, $R^1$, $R^2$ and $R^3$ are selected independently of one another and represent hydrogen or straight-chain or branched alkyl with 1 to 4 carbon atoms, $R^4$, $R^5$ and $R^6$ are selected independently of one another and represent hydrogen, straight-chain or branched alkyl or alkoxy with in either case 1 to 4 carbon atoms, chlorine or hydroxyl, and Z represents chlorine, bromine or iodine.

Very particularly preferred N-pyrimidinylmethyl-haloacetanilides of the formula (I) are those in which $R^1$ represents hydrogen, methyl, ethyl, n-propyl, isopropyl, sec.-butyl or tert.-butyl; $R^2$ represents hydrogen, methyl, ethyl, n-propyl, isopropyl, sec.-butyl or tert.-butyl; $R^3$ represents hydrogen, methyl, ethyl, n-propyl, isopropyl, sec.-butyl or tert.-butyl; $R^4$ represents hydrogen, methyl, ethyl, isopropyl, methoxy, chlorine or hydroxyl; $R^5$ represents hydrogen, methyl, ethyl, isopropyl, methoxy, chlorine or hydroxyl; $R^6$ represents hydrogen, methyl, ethyl, isopropyl, methoxy, chlorine or hydroxyl; and Z represents chlorine or bromine.

The following compounds of the general formula (I) may be mentioned specifically, in addition to the compounds mentioned later in the preparative examples:

TABLE 1

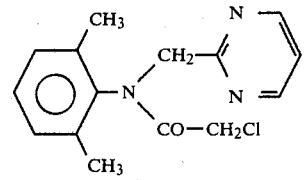

(Ia)

| R¹ | R² | R³ | R⁴ | R⁵ | R⁶ |
|---|---|---|---|---|---|
| 2-C₂H₅ | 6-C₂H₅ | H | H | H | H |
| 2-CH₃ | H | H | H | H | H |
| 2-C(CH₃)₃ | H | H | H | H | H |
| 2-CH₃ | 3-CH₃ | H | H | H | H |
| 2-CH₃ | 5-CH₃ | H | H | H | H |
| 2-CH(CH₃)₂ | H | H | H | H | H |
| 2-CH₃ | 6-CH₃ | H | 4-CH₃ | H | H |
| 2-CH₃ | 6-C₂H₅ | H | 4-CH₃ | H | H |
| 2-C₂H₅ | 6-C₂H₅ | H | 4-CH₃ | H | H |
| 2-CH₃ | H | H | 4-CH₃ | H | H |
| 2-C(CH₃)₃ | H | H | 4-CH₃ | H | H |
| 2-CH₃ | 3-CH₃ | H | 4-CH₃ | H | H |
| 2-CH₃ | 5-CH₃ | H | 4-CH₃ | H | H |
| 2-CH(CH₃)₂ | H | H | 4-CH₃ | H | H |
| 2-CH₃ | 6-CH₃ | H | 4-CH₃ | 6-CH₃ | H |
| 2-CH₃ | 6-C₂H₅ | H | 4-CH₃ | 6-CH₃ | H |
| 2-C₂H₅ | 6-C₂H₅ | H | 4-CH₃ | 6-CH₃ | H |
| 2-CH₃ | H | H | 4-CH₃ | 6-CH₃ | H |
| 2-C(CH₃)₃ | H | H | 4-CH₃ | 6-CH₃ | H |
| 2-CH₃ | 3-CH₃ | H | 4-CH₃ | 6-CH₃ | H |
| 2-CH₃ | 5-CH₃ | H | 4-CH₃ | 6-CH₃ | H |
| 2-CH(CH₃)₂ | H | H | 4-CH₃ | 6-CH₃ | H |
| 2-CH₃ | 6-CH₃ | H | 4-OH | 6-CH₃ | H |
| 2-CH₃ | 6-C₂H₅ | H | 4-OH | 6-CH₃ | H |
| 2-C₂H₅ | 6-C₂H₅ | H | 4-OH | 6-CH₃ | H |
| 2-CH₃ | H | H | 4-OH | 6-CH₃ | H |
| 2-C(CH₃)₃ | H | H | 4-OH | 6-CH₃ | H |
| 2-CH₃ | 3-CH₃ | H | 4-OH | 6-CH₃ | H |
| 2-CH₃ | 5-CH₃ | H | 4-OH | 6-CH₃ | H |
| 2-CH(CH₃)₂ | H | H | 4-OH | 6-CH₃ | H |
| 2-CH₃ | 6-CH₃ | H | 4-OH | 5-OCH₃ | H |
| 2-CH₃ | 6-C₂H₅ | H | 4-OH | 5-OCH₃ | H |
| 2-C₂H₅ | 6-C₂H₅ | H | 4-OH | 5-OCH₃ | H |
| 2-CH₃ | H | H | 4-OH | 5-OCH₃ | H |
| 2-C(CH₃)₃ | H | H | 4-OH | 5-OCH₃ | H |
| 2-CH₃ | 3-CH₃ | H | 4-OH | 5-OCH₃ | H |
| 2-CH₃ | 5-CH₃ | H | 4-OH | 5-OCH₃ | H |
| 2-CH(CH₃)₂ | H | H | 4-OH | 5-OCH₃ | H |
| 2-CH₃ | 6-CH₃ | H | 4-OH | 5-CH₃ | 6-CH₃ |
| 2-CH₃ | 6-C₂H₅ | H | 4-OH | 5-CH₃ | 6-CH₃ |
| 2-C₂H₅ | 2-C₂H₅ | H | 4-OH | 5-CH₃ | 6-CH₃ |
| 2-CH₃ | H | H | 4-OH | 5-CH₃ | 6-CH₃ |
| 2-C(CH₃)₃ | H | H | 4-OH | 5-CH₃ | 6-CH₃ |
| 2-CH₃ | 3-CH₃ | H | 4-OH | 5-CH₃ | 6-CH₃ |
| 2-CH₃ | 5-CH₃ | H | 4-OH | 5-CH₃ | 6-CH₃ |
| 2-CH(CH₃)₃ | H | H | 4-OH | 5-CH₃ | 6-CH₃ |
| 2-CH₃ | 6-CH₃ | H | 4-CH₃ | 5-Cl | 6-OH |
| 2-CH₃ | 6-C₂H₅ | H | 4-CH₃ | 5-Cl | 6-OH |
| 2-C₂H₅ | 6-C₂H₅ | H | 4-CH₃ | 5-Cl | 6-OH |
| 2-CH₃ | H | H | 4-CH₃ | 5-Cl | 6-OH |
| 2-C(CH₃)₃ | H | H | 4-CH₃ | 5-Cl | 6-OH |
| 2-CH₃ | 3-CH₃ | H | 4-CH₃ | 5-Cl | 6-OH |
| 2-CH₃ | 5-CH₃ | H | 4-CH₃ | 5-Cl | 6-OH |
| 2-CH(CH₃)₂ | H | H | 4-CH₃ | 5-Cl | 6-OH |

If, for example, N-(pyrimidin-2-yl-methyl)-2,6-dimethyl-aniline and chloroacetyl chloride are used as starting substances, the course of the reaction can be represented by the following equation:

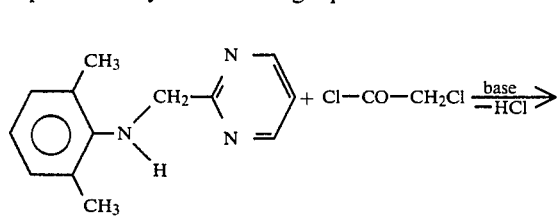

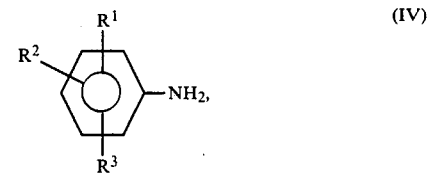

The formula (II) provides a general definition of the N-pyrimidinylmethyl-anilines required as starting substances in carrying out the process according to the invention. In this formula, R¹, R², R³, R⁴, R⁵ and R⁶ preferably have those meanings which have already been mentioned as preferred for these radicals in connection with the description of the substances of the formula (I).

The N-pyrimidinylmethyl-anilines of the formula (II) have not hitherto been disclosed in the literature. They are obtained when anilines of the general formula

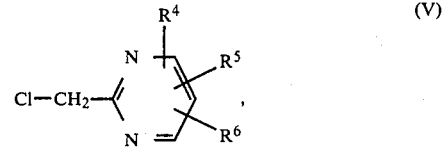

in which

R¹, R² and R³ have the meanings indicated above, are reacted with pyrimidin-2-yl-methyl chlorides of the general formula (V)

Cl—CH₂—[pyrimidinyl with R⁴, R⁵, R⁶]

in which

R⁴, R⁵ and R⁶ have the meanings indicated above, in the presence of an acid-binding agent and if appropriate in the presence of a diluent.

The anilines of the formula (IV) required as starting substances in the preparation of the N-pyrimidinylmethyl-anilines of the formula (II) are generally known compounds of organic chemistry. Examples which may be mentioned are given in the following table:

TABLE 2

(IV)

| R¹ | R² | R³ | R¹ | R² | R³ |
|---|---|---|---|---|---|
| H | H | H | 2-CH₃ | 6-C₄H₉—sec. | H |
| 2-CH₃ | H | H | 2-CH₃ | 6-C₄H₉—sec. | H |
| 2-C₂H₅ | H | H | 3-CH₃ | 5-CH₃ | H |
| 2-CH₃ | 6-CH₃ | H | 2-CH₃ | 4-C₂H₅ | 6-CH₃ |
| 2-CH₃ | 6-C₂H₅ | H | 2-C₂H₅ | 4-CH₃ | 6-C₂H₅ |
| 2-C₂H₅ | 6-C₂H₅ | H | 2-C₂H₅ | 3-CH₃ | 6-C₂H₅ |
| 2-CH₃ | 3-CH₃ | H | 2-C₂H₅ | 4-CH₃ | 6-CH₃ |

TABLE 2-continued $$R^2 \underset{R^3}{\overset{R^1}{\diagdown}} \!\!\! \bigcirc \!\!\! -NH_2 \quad (IV)$$

| R$^1$ | R$^2$ | R$^3$ | R$^1$ | R$^2$ | R$^3$ |
|---|---|---|---|---|---|
| 2-C$_2$H$_5$ | 3-CH$_3$ | H | 2-C$_3$H$_7$i | H | H |
| 2-CH$_3$ | 6-C$_3$H$_7$i | H | 2-C$_3$H$_7$i | 6-C$_3$H$_7$i | H |
| 2-C$_2$H$_5$ | 4-CH$_3$ | H | 2-C(CH$_3$)$_3$ | 4-CH$_3$ | H |
| 2-C$_3$H$_7$i | 3-CH$_3$ | H | 2-C$_3$H$_7$n | H | H |
| 2-C$_3$H$_7$i | 4-CH$_3$ | H | 2-C$_4$H$_9$—sec. | H | H |
| 2-C$_3$H$_7$i | 4-CH$_3$ | 6-C$_3$H$_7$i | 2-C$_4$H$_9$—sec. | 6-C$_4$H$_5$—sec. | H |
| 2-C$_3$H$_7$i | 6-C$_2$H$_5$ | H | 2-C$_4$H$_9$—sec. | 6-C$_2$H$_5$ | H |
| 2-C$_3$H$_7$i | 6-CH$_3$ | H | 2-C(CH$_3$)$_3$ | H | H |

The pyrimidin-2-yl-methyl chlorides of the formula (V) also required as starting substances in the preparation of the N-pyrimidinylmethyl-anilines of the formula (II) are known from, for example, U.S. Pat. No. 3,118,889, J. Amer. Chem. Soc. 68, 2393 (1946), Z. obsc. Chim. 34, 2164 (1964), Z. obsc. Chim. 32, 2431 (1962), Z. obsc. Chim. 33, 2848 (1963) and J. Med. Chem. 7, 808 (1964), or they can be prepared by the processes indicated in these publications. Thus, unsubstituted pyrimidin-2-yl-methyl chloride is obtained when chloroacetamidine hydrochloride (see J. Org. Chem. 26, 412 (1967)) is reacted with tetramethoxypropane. The alkyl-substituted pyrimidin-2-yl-methyl chlorides of the formula (II) can be obtained by reacting chloroacetamidine hydrochloride, which is known, with corresponding acyl ketones, acylaldehydes or acetals thereof, for example acetylacetone or 3-ketobutyraldehyde dimethyl acetal. The hydroxy-substituted pyrimidin-2-yl-methyl chlorides of the formula (II) can be obtained by reacting chloroacetamidine hydrochloride with ketocarboxylic acid esters, for example acetoacetic acid esters of malonic acid esters, it being possible for the hydroxyl groups to be replaced by halogen, especially chlorine, in the customary manner, for example by further reaction with phosphorus oxychloride or thionyl chloride.

The halogen-substituted pyrimidin-2-yl-methyl chlorides of the formula (II) can also be obtained directly, by halogenating optionally alkyl- and/or hydroxy-substituted pyrimidin-2-yl-methyl chlorides of the formula (II) in the customary manner, for example by reaction with hypochlorite solution, chlorine in carbon tetrachloride or sulphuryl chloride.

The alkoxy-substituted pyrimidin-2-yl-methyl chlorides of the formula (II) can be obtained, for example, by reacting chloroacetamidine hydrochloride with α-alkoxy-α-formyl-acetic acid esters, for example α-methoxy-α-formyl-acetic acid methyl ester, in the customary manner.

The following compounds of the general formula (V) may be mentioned specifically, in addition to the compounds mentioned later in the preparative examples:

TABLE 3

$$Cl-CH_2-\underset{N=}{\overset{N}{\diagup}} \!\!\! \underset{R^6}{\overset{R^5}{\diagdown}} \quad (V)$$

| R$^4$ | R$^5$ | R$^6$ |
|---|---|---|
| 4-CH$_3$ | 6-Cl | H |
| 4-OH | 6-OH | H |
| 4-Cl | 6-Cl | H |
| 4-Cl | H | H |

Any of the customary organic and inorganic acid acceptors can be used as the acid-binding agent in the preparation of the N-pyrimidinylmethyl-anilines of the formula (II) by the process indicated above. Acid acceptors which are preferably used are: alkali metal carbonates, such as potassium carbonate or sodium carbonate; tertiary amines, such as triethylamine; or pyridine.

Any of the customary inert organic solvents can be employed as diluents in the preparation of the N-pyrimidinylmethyl-anilines of the formula (II). Dimethylformamide and toluene are preferably used.

The reaction temperatures can be varied within a substantial range in the preparation of the N-pyrimidinylmethyl-anilines of the formula (II) by the above process. In general, the reaction is carried out at between 0° and 180° C., preferably between 20° and 150° C.

The anilines of the formula (IV) and the pyrimidin-2-yl-methyl chlorides of the formula (V) are in general employed in equimolar amounts in the preparation of the N-pyrimidinylmethyl-anilines of the formula (II) by the above process. However, it is also possible to employ one of the components, preferably the aniline of the formula (IV), in excess.

The reaction products are worked up and isolated by customary methods (see also the preparative examples).

The formulae (IIIa) and (IIIb) provide general definitions of the haloacetic acid chlorides, bromides and anhydrides also to be used as starting substances for the process according to the invention. In these formulae, Z preferably represents chlorine, bromine or iodine.

The haloacetic acid chlorides, bromides and anhydrides of the formulae (IIIa) and (IIIb) are generally known compounds of organic chemistry. Examples which may be mentioned are: chloroacetyl chloride, bromoacetyl chloride, iodoacetyl chloride and the corresponding bromides and anhydrides.

Preferred diluents for the reaction according to the invention are inert organic solvents. These include, as preferences, ketones, such as diethyl ketone, and in particular acetone and methyl ethyl ketone; nitriles, such as propionitrile and in particular acetonitrile; ethers, such as tetrahydrofuran or dioxan; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

If appropriate, the process according to the invention can be carried out in the presence of an acid-bidning agent. Any of the customary acid-binding agents can be used as these agents. These include, as preferences, organic bases, such as tertiary amines, for example triethylamine, or pyridine, and furthermore inorganic bases, for example alkali metal hydroxides and alkali metal carbonates.

The reaction temperatures can be varied within a substantial range in carrying out the process according to the invention. In general, the reaction is carried out at between 0° C. and 120° C., preferably between 20° C. and 100° C.

In carrying out the process according to the invention, 1 to 1.5 moles of halogenating agent and 1 to 1.5 moles of acid-binding agent are preferably employed per mole of the compound of the formula (II). Isolation of the compounds of the formula (I) is effected in the customary manner.

The active compounds according to the invention influence plant growth and can therefore be used as defoliants, desiccants, agents for destroying plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestions, decoractive tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the invention are particularly suitable for selective use in Beta (beet), rape-seed and other Brassicaceae, soya bean and other Leguminosae, and in maize and cotton.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is, liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomizing or scattering.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 10 kg of active compound per hectare, preferably between 0.25 and 5 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Example.

In this Example, the compounds according to the present invention are each identified by the number (given in brackets) of the corresponding preparative Example, which will be found later in this specification.

The known comparison compound is identified as follows:

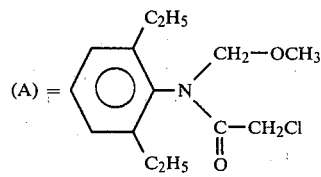

(2,6-Diethyl)-N-methoxymethyl-chloroacetanilide

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0% = no action (like untreated control)
100% = total destruction

In this test, the active compound (5) exhibited a better selectively herbicidal activity than the substance (A) known from the prior art.

PREPARATIVE EXAMPLES

EXAMPLE 1

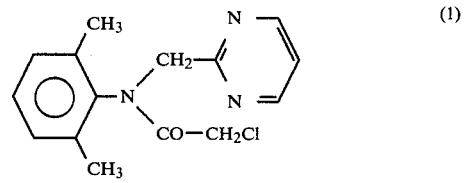

8.5 g (0.04 mol) of N-(pyrimidin-2-yl-methyl)-2,6-dimethylaniline and 3.2 g (0.04 mol) of pyridine were heated under reflux in 20 ml of tetrahydrofuran. 4.5 g (0.04 mol) of chloroacetyl chloride were added dropwise to this mixture. The reaction mixture was stirred under reflux for 5 hours and then poured onto 300 g of ice. The crystalline precipitate formed was filtered off, washed with water and recrystallized from carbon tetrachloride. 8.2 g (71% of theory) of 2,6-dimethyl-N-(pyrimidin-2-yl-methyl)-chloroacetanilide were obtained in the form of colorless crystals of melting point 110° C.

Preparation of the precursors

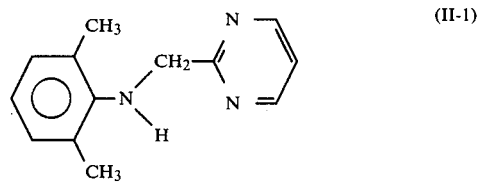

48.4 g (0.4 mol) of 2,6-dimethylaniline, 55.3 g (0.4 mol) of potassium carbonate and 0.2 g of potassium iodide were heated to 100° C. in 60 ml of dimethylformamide, and 25.7 g (0.2 mol) of 2-chloromethyl-pyrimidine were then added dropwise. The reaction mixture was subsequently stirred at 100° C. for 5 hours and then poured onto 500 g of ice. It was then extracted three times with 150 ml of methylene chloride each time. The combined organic phases were dried over sodium sulphate and concentrated in vacuo. The residue was distilled under a high vacuum. 30 g (70% of theory) of N-(pyrimidin-2-yl-methyl)-2,6-dimethylaniline were obtained as a colorless oil of boiling point 150° C./0.2 mm Hg.

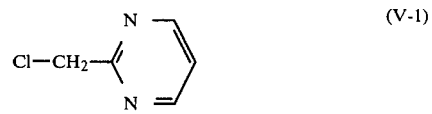

141.9 g (1.1 mol) of chloroacetamidine hydrochloride and 69 g (0.5 mol) of potassium carbonate were heated to 80° C. in 200 ml of toluene. 164 g (1 mol) of 1,3-tetramethoxypropane were then added dropwise. During this addition, the methanol formed was distilled off, and the mixture was then heated, while increasing the bath temperature and heating the toluene entrained from the reaction vessel up to the boiling point of pure toluene. The toluene was decanted and a black crystalline mass was obtained and was boiled up twice more with 200 ml of toluene each time. The toluene extracts were evaporated in vacuo and the residue thereby obtained was distilled under a high vacuum. 45 g (35% of theory) of 2-chloromethylpyrimidine were obtained as a colorless oil of boiling point 34° C./0.2 mm Hg.

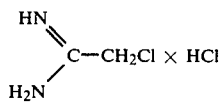

4.6 g (0.2 mol) of sodium were dissolved in 500 ml of methanol. 151 g (2 mol) of chloroacetonitrile were added dropwise, while cooling the mixture to about 20° C., and the mixture was then subsequently stirred at room temperature for 1 hour. 117.7 g (2.2 mol) of ammonium chloride were then added in portions and the mixture was again subsequently stirred for one hour. The solution was then evaporated in vacuo. The residue was stirred with ether, filtered off and rinsed with ether.

255 g (99% of theory) of chloroacetamidine hydrochloride were obtained in the form of dark crystals of melting point 98° C.

Those compounds listed by their formulae in Table 4 were obtained in a manner analogous to that in Example 1.

TABLE 4

(I)

| Example No. | $R^1$ | $R^2$ | $R^3$ | $R^4$ | $R^5$ | $R^6$ | Z | Melting point (°C.) |
|---|---|---|---|---|---|---|---|---|
| 2 | H | H | H | H | H | H | Cl | 67 |
| 3 | H | H | H | 4-CH$_3$ | H | H | Cl | 97 |
| 4 | 2-CH$_3$ | 6-CH$_3$ | H | 4-CH$_3$ | 6-CH$_3$ | H | Cl | 105 |
| 5 | 2-CH$_3$ | 6-C$_2$H$_5$ | H | H | H | H | Cl | 68 |

The starting materials of the formula (II) listed by their formulae in Table 5 which follows were obtained by the process described in the Application and analogously to the procedure described after Example 1:

TABLE 5

(II)

| Example No. | $R^1$ | $R^2$ | $R^3$ | $R^4$ | $R^5$ | $R^6$ | Melting point (°C.) or boiling point (°C./mm Hg) |
|---|---|---|---|---|---|---|---|
| (II-2) | H | H | H | H | H | H | 58 |
| (II-3) | H | H | H | 4-CH$_3$ | H | H | 48 |
| (II-4) | 2-CH$_3$ | 6-CH$_3$ | H | 4-CH$_3$ | 6-CH$_3$ | H | 147/0.15 |
| (II-5) | 2-CH$_3$ | 6-C$_2$H$_5$ | H | H | H | H | 145–147/0.4 |
| (II-6) | 2-CH$_3$ | 6-CH$_3$ | H | H | H | H | 150/0.2 |

The starting materials of the formula (V) listed by their formulae in Table 6 which follows were obtained by the processes described in the Application:

TABLE 6

(V)

| Example No. | $R^4$ | $R^5$ | $R^6$ | Melting point (°C.) or boiling point (°C./mm Hg) |
|---|---|---|---|---|
| (V-2) | 4-CH$_3$ | 6-CH$_3$ | H | 60 |
| (V-3) | 4-CH$_3$ | H | H | 40/0.1 |
| (V-4) | 4-CH$_3$ | 6-OH | H | 160 |
| (V-5) | 4-OH | 5-Cl | 6-CH$_3$ | 179 |
| (V-6) | 4-OH | 5-CH$_3$ | 6-CH$_3$ | 267 |
| (V-7) | 4-Cl | 5-Cl | 6-Cl | 120/6 |
| (V-8) | 4-Cl | 5-CH$_3$ | 6-Cl | 40 |
| (V-9) | 4-OH | 5-OCH$_3$ | H | 138 |

It will be understood that the specification and examples are illustrative, but not limitative of the present invention and that other embodiments within the spirit and scope of the invention will suggest themselves to those skilled in the art.

What is claimed is:

1. N-pyrimidinylmethyl-haloacetanilide compound of the formula

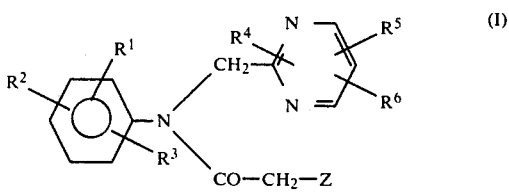

wherein
$R^1$ is hydrogen or alkyl with 1 to 4 carbon atoms;
$R^2$ is hydrogen or alkyl with 1 to 4 carbon atoms;
$R^3$ is hydrogen or alkyl with 1 to 4 carbon atoms;

R[4] is hydrogen, alkyl with 1 to 4 carbon atoms, alkoxy with 1 to 4 carbon atoms, chlorine or hydroxyl;

R[5] is hydrogen, alkyl with 1 to 4 carbon atoms, alkoxy with 1 to 4 carbon atoms, chlorine or hydroxyl;

R[6] is hydrogen, alkyl with 1 to 4 carbon atoms, alkoxy with 1 to 4 carbon atoms, chlorine or hydroxyl; and Z is chlorine, bromine or iodine.

2. Compounds as claimed in claim 1 wherein R[1] is hydrogen.

3. Compounds as claimed in claim 1 wherein R[1] is alkyl of 1 to 4 carbon atoms.

4. Compounds as claimed in claim 1 wherein R[2] is hydrogen.

5. Compounds as claimed in claim 1 wherein R[2] is alkyl of 1 to 4 carbon atoms.

6. Compounds as claimed in claim 1 wherein R[3] is hydrogen.

7. Compounds as claimed in claim 1 wherein R[3] is alkyl of 1 to 4 carbon atoms.

8. Compounds as claimed in claim 1 wherein R[4] is hydrogen.

9. Compounds as claimed in claim 1 wherein R[4] is alkyl of 1 to 4 carbon atoms.

10. Compounds as claimed in claim 1 wherein R[4] is chlorine or bromine.

11. Compounds as claimed in claim 1 wherein R[4] is alkoxy with 1 to 4 carbon atoms.

12. Compounds as claimed in claim 1 wherein R[4] is hydroxyl.

13. Compounds as claimed in claim 1 wherein R[5] is hydrogen.

14. Compounds as claimed in claim 1 wherein R[5] is alkyl of 1 to 4 carbon atoms.

15. Compounds as claimed in claim 1 wherein R[5] is chlorine or bromine.

16. Compounds as claimed in claim 1 wherein R[5] is alkoxy with 1 to 4 carbon atoms.

17. Compounds as claimed in claim 1 wherein R[5] is hydroxyl.

18. Compounds as claimed in claim 1 wherein R[6] is hydrogen.

19. Compounds as claimed in claim 1 wherein R[6] is alkyl with 1 to 4 carbon atoms.

20. Compounds as claimed in claim 1 wherein R[6] is chlorine or bromine.

21. Compounds as claimed in claim 1 wherein R[6] is alkoxy of 1 to 4 carbon atoms.

22. Compounds as claimed in claim 1 wherein R[6] is hydroxyl.

23. Compounds as claimed in claim 1 wherein Z is chlorine or bromine.

24. N-pyrimidinylmethyl-haloacetanilide compound of the formula wherein

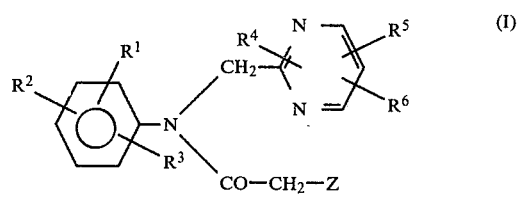

R[1] is hydrogen, methyl, ethyl, n-propyl, isopropyl, sec-butyl or tert.-butyl;

R[2] is hydrogen, methyl, ethyl, n-propyl, isopropyl, sec.-butyl or tert.-butyl;

R[3] is hydrogen, methyl, ethyl, n-propyl, isopropyl, sec.-butyl or tert.-butyl;

R[4] is hydrogen, methyl, ethyl, isopropyl, methoxy, chlorine or hydroxyl;

R[5] is hydrogen, methyl, ethyl, isopropyl, methoxy, chlorine or hydroxyl;

R[6] is hydrogen, methyl, ethyl, isopropyl, methoxy, chlorine or hydroxyl; and

Z is chlorine or bromine.

25. N-pyrimidinylmethyl-haloacetanilide compound designated 2,6-dimethyl-N-(pyrimidin-2-yl-methyl)-chloroacetanilide.

26. N-pyrimidinylmethyl-haloacetanilide compound designated N-(pyrimidin-2-yl-methyl)-chloroacetanilide.

27. N-pyrimidinylmethyl-haloacetanilide compound designated N-(4-methylpyrimidin-2-yl-methyl)-chloroacetanilide.

28. N-pyrimidinylmethyl-haloacetanilide compound designated 2,6-dimethyl-N-(4,6-dimethyl pyrimidin-2-yl-methyl)-chloroacetanilide.

29. N-pyrimidinylmethyl-haloacetanilide compound designated 2-methyl-6-ethyl-N-(pyrimidin-2-yl-methyl)-chloroacetanilide.

30. Herbicidal composition comprising a herbicidally acceptable carrier and, in herbicidally effective amounts, an N-pyrimidinylmethyl-haloacetanilide compound as claimed in claim 1.

31. Herbicidal composition as claimed in claim 30 containing from 0.1 to 95% of the active compound, by weight.

32. Method of combating weeds, which method comprises applying to the weeds, or their habitat, a herbicidally effective amount of an N-pyrimidinylmethyl-haloacetanilide compound as claimed in claim 1.

33. Method as claimed in claim 32 wherein said compound is applied to an area of agriculture in an amount of 0.1 to 10 kg per hactare.

34. Method as claimed in claim 32 wherein said compound is applied to an area of agriculture in an amount of 0.25 to 5 kg per hectare.

35. Method of combating weeds comprising applying to the weeds, or their habitat, a herbicidally effective amount of an N-pyrimidinylmethyl-haloacetanilide compound selected from 2,6-dimethyl-N-(pyrimidin-2-yl-methyl)-chloroacetanilide;

N-(pyrimidin-2-yl-methyl)-chloroacetanilide;

N-(4-methylpyrimidin-2-yl-methyl)-chloroacetanilide;

2,6-dimethyl-N-(4,6-dimethyl-pyrimidin-2-yl-methyl)-chloroacetanilide; and 2-methyl-6-ethyl-N-(pyrimidin-2-yl-methyl)-chloroacetanilide.

* * * * *